United States Patent [19]

Sudhakar

[11] Patent Number: 5,442,093
[45] Date of Patent: Aug. 15, 1995

[54] PROCESS FOR PREPARING INTERMEDIATES FOR THE SYNTHESIS OF ANTIFUNGAL AGENTS

[75] Inventor: Anantha Sudhakar, East Brunswick, N.J.

[73] Assignee: Schering Corporation, Kenilworth, N.J.

[21] Appl. No.: 239,488

[22] Filed: May 9, 1994

[51] Int. Cl.$^6$ .............................................. C07C 69/76
[52] U.S. Cl. ........................................................ 560/82
[58] Field of Search ............................................. 560/82

[56] References Cited

U.S. PATENT DOCUMENTS 5,039,676  8/1991  Saksena et al. .

FOREIGN PATENT DOCUMENTS

WO89/04829  6/1989  WIPO .
WO93/09114  5/1993  WIPO .

OTHER PUBLICATIONS

Advance Organic Chemistry, 3rd Edition, Mar., 1985, pp. 642–643.

Ahmar, et al., *Tet. Lett.*, 25, (No. 40) 4505–4508 (1984).
Ahmar, et al., *Tetrahedron*, 43, (No. 3) 513–526 (1987).
Brenda, et al., *Syn. Lett.*, (No. 11) 809–810 (1991).
Coulson, *J. Org. Chem.*, 38, (No. 8) 1483–1490 (1973).
Austin, et al., *J. Org. Chem.*, 46, 2280–2286 (1981).

*Primary Examiner*—José G. Dees
*Assistant Examiner*—Samuel Barts
*Attorney, Agent, or Firm*—Paul A. Thompson

[57] ABSTRACT

Disclosed is a process for preparing compounds of the formula I

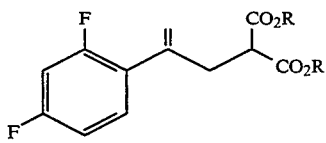

wherein R is $C_1$–$C_6$ alkyl, comprising heating a mixture of a difluorobenzene derivative, allene, a dialkyl malonate of the formula $CH_2(CO_2R)_2$, wherein R is $C_1$–$C_6$ alkyl, and a base, in a polar organic solvent in the presence of a catalyst.

13 Claims, No Drawings

PROCESS FOR PREPARING INTERMEDIATES FOR THE SYNTHESIS OF ANTIFUNGAL AGENTS

BACKGROUND OF THE INVENTION

The present invention comprises a chemically efficient one step process for the synthesis of intermediates useful in the synthesis of antifungal agents.

PCT International Publication No. WO 89/04829, U.S. Pat. No. 5,039,676, and PCT International Publication No. WO 93/09114 disclose substituted tetrahydrofuran azole compounds having utility as antifungal agents. A number of processes for the synthesis of these compounds are known. In particular, co-owned, co-pending U.S. Ser. No. 08/055,268 describes a process for preparing chiral intermediates for use in the preparation of these antifungal agents. Dialkyl malonate derivatives of the formula I

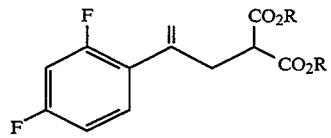

wherein R is $C_1-C_6$ alkyl, are important intermediates used in this process. An efficient synthesis of compounds of the formula I is therefore a key factor in the synthesis of antifungal compounds via this process.

U.S. Ser. No. 08/055,268 discloses a process for preparing compounds of the formula I. This process, as shown in Reaction 1, comprises reacting a dialkyl malonate anion, wherein $M^+$ is a suitable metal counterion and R is $C_1-C_6$ alkyl, with a compound of the formula II, wherein Z is a leaving group selected from Br, $-OSO_2CH_3$ or $-OSO_2C_6H_4CH_3$, to form a compound of formula I. However, the process is inefficient in that a multistep process is necessary to prepare the starting compounds of formula II.

Reaction 1:

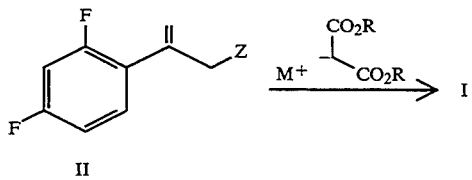

The carbopalladation of allenes is disclosed by Ahmar, et al in *Tetrahedron*, 43(3), 513-526 (1987) and Ahmar, et al in *Tet. Lett.*, 25 (40), 4505-4508 (1984). The Ahmar et al publications disclose carbopalladation reactions involving iodobenzene, allene and sodio diethyl malonate to form a compound of the formula IV

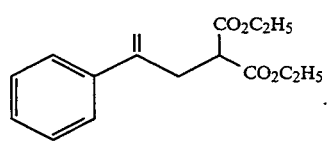

The Ahmar et al publications also teach such reactions using bromobenzene and 1,2-decadiene.

SUMMARY OF THE INVENTION

The present invention comprises a process for preparing compounds of the formula I

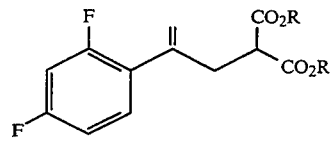

wherein R is $C_1-C_6$ alkyl, comprising heating a mixture of a difluorobenzene derivative of the formula (IX)

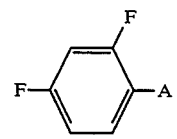

wherein A is Br, I, $-OS(O)_2R^2$, or $-OP(=O)(OR^3)_2$, and wherein $R^2$ is F, $CF_3$, $C_1-C_6$ alkyl, aryl or substituted aryl, and $R^3$ is $C_1-C_6$ alkyl, with allene, a dialkyl malonate of the formula $CH_2(CO_2R)_2$, wherein R is $C_1-C_6$ alkyl, and a base, in a polar organic solvent in the presence of a catalyst to form the compound of formula I.

Preferably A is Br, I, $-OS(O)_2R^2$ or $-OP(=O)-(OR^3)_2$, wherein $R^2$ is F, $CF_3$, $CH_3$, $C_6H_5$, $-C_6H_4CH_3$, $-C_6H_4CF_3$ or naphthyl, and $R^3$ is $CH_3$ or $C_2H_5$. Preferably R is ethyl or methyl and the catalyst is a Palladium catalyst. Preferably the base is $K_2CO_3$, $Na_2CO_3$, NaH, KH, $NaOR^1$ or $KOR^1$, wherein $R^1$ is $C_1-C_6$ alkyl, or a phosphate salt, such as $Na_3PO_4$ or $K_3PO_4$. Preferred solvents include DMF, DMSO, THF, acetone and acetonitrile.

More preferred is a process as described above wherein the base is $Na_3PO_4$ or $K_3PO_4$, and the catalyst is selected from Pd(dppe), $Pd(PPh_3)_4$, $PdCl_2(PPh_3)_2$. Also more preferred are palladium catalysts selected from $Pd_2(dba)_3$ and $PdX_2$, wherein X is Cl, Br or I, which catalysts are used in combination with a triarylphosphine of the formula $P(Ar)_3$, wherein Ar is an aryl group selected from phenyl or ortho-tolyl. Most preferably the catalyst is $PdCl_2(PPh_3)_2$. Most preferably A is Br. Preferably the mixture is heated to 40° to 120° C., and most preferably to 60° to 80° C.

DETAILED DESCRIPTION

As used herein, the term:

"aryl" means a carbocyclic aromatic group, such as phenyl or naphthyl;

"substituted aryl" means an aryl group having 1, 2 or 3 substituents independently selected from F, Cl, Br, $CF_3$ or $C_1-C_6$ alkyl.

"polar organic solvent" means an organic solvent that is water miscible and is able to solubilize ionic species, with preferred solvents including DMF, DMSO, THF, acetone and $CH_3CN$; and "base" means a reagent capable of deprotonating a dialkyl malonate to form the corresponding malonate salt. Preferred bases include $K_2CO_3$, $Na_2CO_3$, NaH, KH, $NaOR^1$ or $KOR^1$, wherein $R^1$ is $C_1-C_6$ alkyl, or a phosphate salt, such as $Na_3PO_4$ or $K_3PO_4$.

The catalyst of the present invention is a palladium reagent, preferably a Pd(0) or Pd(II) compound capable of catalyzing the carbopalladation of allene to form an intermediate π-allyl Pd complex which subsequently reacts with a malonate anion nucleophile to form a compound of the formula I. Preferred is a catalyst selected from: 1,2-bis-(diphenylphosphino)ethanepalladium(O), (Pd(dppe)); tetrakis(triphenylphosphine)palladium(O), (Pd(PPh₃)₄); bis(triphenylphosphine)palladium(II) chloride, (PdCl₂(PPh₃)₂); or a combination of a phosphine of the formula P(Ar)₃, wherein Ar is an aryl group selected from phenyl or ortho-tolyl, and either tris(dibenzylideneacetone)-dipalladium(O), (Pd₂(dba)₃), or PdX₂, wherein X is Cl, Br or I.

The following solvents, reagents and ligands employed in the process of the present invention are identified by the abbreviations indicated: dimethylformamide (DMF); tetrahydrofuran (THF); dimethylsulfoxide (DMSO); triphenylphosphine (PPh₃); 1,2-bis-(diphenylphosphino)ethane (dppe); dibenzylideneacetone (dba).

The present invention comprises a process as shown in Reaction A for preparing compounds of the formula I.

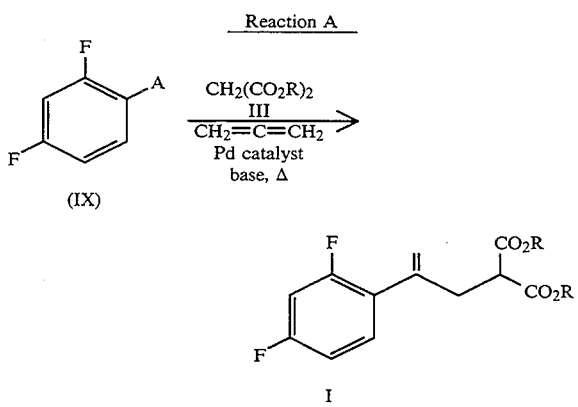

In Reaction A, the dialkyl malonate III is treated with base, preferably NaH or KH, to pre-form the malonate anion sodium or potassium salt. The malonate salt, difluorobenzene derivative (IX), preferably 1-bromo-2,4-difluorobenzene, polar organic solvent, preferably THF, the catalyst and allene are then combined and heated to 40° to 100° C., preferably 50° to 90° C., and most preferably 70° to 80° C., in a sealed vessel under pressure of 1–30 psig, preferably at 5–15 psig, to form the dialkyl malonate derivative I.

Alternatively, in Reaction A, the dialkyl malonate III is combined with the difluorobenzene derivative (IX), base, polar organic solvent, and catalyst. The base is preferably Na₂CO₃, K₂CO₃, Na₃PO₄ or K₃PO₄, and most preferably Na₃PO₄. The polar organic solvent is preferably DMF, DMSO, THF, acetone or CH₃CN, and most preferably DMF. The catalyst is preferably Pd(dppe), Pd(PPh₃)₄, PdCl₂(PPh₃)₂, or a combination of P(Ar)₃ and either Pd₂(dba)₃ or PdX₂, wherein Ar and X are as defined above, and more preferably PdCl₂(PPh₃)₂. The resulting mixture is heated to 40° to 120° C., preferably to 50° to 90° C., and most preferably 70° to 80° C., and pressurized with allene to 1–30 psig, preferably 1–15 psig, and most preferably 1–10 psig. Heating is maintained until about 1.3 equivalents of allene have been consumed. The mixture is then cooled to room temperature, quenched with dilute acid, such as aqueous H₂SO₄, and extracted with a suitable solvent, such as heptane, to give the compound of formula I.

The starting difluorobenzene derivatives (IX), such as 1-bromo-2,4-difluorobenzene, are known and are commercially available or can be prepared by established methods. For example, compounds of the formula (IX) wherein A is —OS(O)₂R², or —OP(=O)(OR³)₂ can be prepared from commercially available 2,4-difluorophenol via established methods.

The following preparations and examples are illustrative of the process of the present invention.

EXAMPLE 1

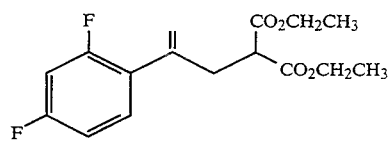

Combine 1 g of bis(triphenylphosphine)palladium (II) chloride, 300 mL of DMF, 100 g of 1-bromo-2,4-difluorobenzene, 165 mL of diethyl malonate and 210 g of Na₃PO₄ in a sealed vessel under nitrogen atmosphere (1 psig). Heat the mixture to 75° C. and add slowly 26 g of allene at a rate such that the pressure remains below 10 psig. Continue heating at 70°–75° C. for 24 h. Cool to room temperature, then slowly pour the mixture into 50 mL of concentrated H₂SO₄ and 500 mL of water. Extract with 600 mL of heptane and wash the heptane extract with water (2×100 mL). Distill the extract to concentrate to a volume of 300 mL. Add 5 g of maleic anhydride and heat the mixture at reflux for 4 h. Cool to room temperature, add 400 mL of water and 30 g of K₂CO₃, then stir for 3 h. Separate the layers, wash the heptane layer with water (2×100 mL), then concentrate the heptane solution to a residue to give 139 g of the title compound.

In the foregoing Example, the maleic anhydride treatment serves to remove a diene impurity of the formula (V)

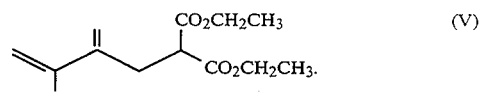

The diene (V) reacts with the maleic anhydride to form an anhydride, which in turn is hydrolyzed by the subsequent treatment with aqueous base to form the dianion (VI) as shown in Reaction 2. Compound (VI) remains in aqueous solution. Compound VIII (see Example 2 below) undergoes the same reaction and, to the extent that it may be present, is also removed via maleic anhydride/aqueous base treatment.

Reaction 2:

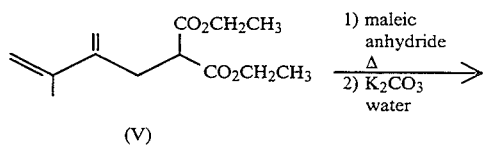

Reaction 2:

-continued

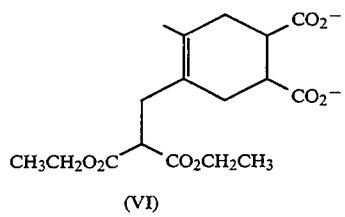

(VI)

The title compound of Example 1 was also prepared using the base, catalyst and solvent shown in Table 1 by following substantially the same procedure as described in Example 1.

TABLE 1

| Example | Catalyst | Base | Solvent |
|---|---|---|---|
| 1A | $Pd_2(dba)_3$ + dppe | $K_2CO_3$ | acetone |
| 1B | $Pd_2(dba)_3$ + dppe | $K_2CO_3$ | DMF |
| 1C | $Pd_2(dba)_3$ + $PPh_3$ | $K_2CO_3$ | DMF |
| 1D | $PCl_2(PPh_3)_2$* | $K_2CO_3$ | DMF |

*Initial reaction pressure after charging allene was 43 psi at 70° C.

EXAMPLE 2

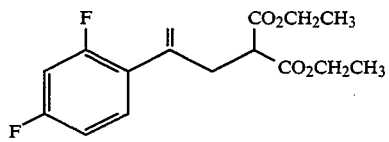

A series of experiments were performed by combining 2,4-difluorobromobenzene, 1-2 equivalents of diethyl malonate and a base, with a solution of palladium catalyst in a suitable vessel. The catalyst was $PdCl_2(Ph_3)_2$ (1-3% by weight), with the exception of experiment 2A, where $PdCl_2$/dppe was used as the catalyst. In most experiments, the vessel was sealed, purged with nitrogen gas, and then evacuated. Allene was then charged to the evacuated vessel, the mixture heated to about 72° C., and the initial pressure recorded.

Alternatively, in experiments 2P, 2Q, 2S and 2T, allene was charged to an evacuated chilled gas sample tube equipped with a regulator. The allene was then charged to the heated reaction vessel (about 72° C.) at a pressure of 3 psig. In either circumstance, heating was then maintained for 16-24 h, and the reaction mixture analyzed by HPLC (Zorbax®RX-C-8 column, 75:25 MeOH/water, 1 mL/min).

The specific reaction conditions and results of these experiments are summarized in Table 2. These results include the percentage of each of the following eight compounds as determined by HPLC:

title compound, i.e., compound I wherein R is ethyl, having a retention time of 7.8min.;

unreacted starting material (S.M.), having a retention time of 5.3 min.;

the diene impurity, e.g. compound V, having a retention time of 6.8 min.;

an impurity identified as compound VII, having the structural formula

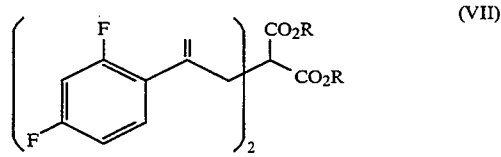

and having a retention time of 19.6 min.;

an impurity identified as compound VIII, having the structural formula

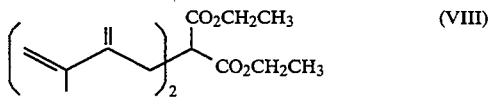

and having a retention time of 18.3 min,; and three unidentified impurities, denoted A, B and C, having retention times of 7.2 min., 12.3 min. and 22.8 min., respectively.

TABLE 2

| | Reaction Conditions | | | | | | HPLC analysis of products | | | | | | | |
|---|---|---|---|---|---|---|---|---|---|---|---|---|---|---|
| Ex. # | 1-Br-2,4-di-F—$C_6H_3$ | Solvent | Mol % allene | Init. Press. at 72° C. (psig) | Base | Mol % base | % I | % S.M. | % V | % VII | % VIII | % A | % B | % C |
| 2A | 10 g | DMF | 120 | 20 | $K_2CO_3$ | 3.25 | 70.2 | 3.0 | 6.6 | 15.3 | 0 | 0 | 2.8 | 1.9 |
| 2B | 10 g | DMSO | 120 | 20 | $K_2CO_3$ | 3.25 | 35.8 | 32.4 | 3.4 | 21.7 | 0 | 4.1 | 2.5 | 0 |
| 2C | 10 g | acetone | 111 | 30 | $K_2CO_3$ | 3.25 | 70.7 | 5.4 | 0.6 | 11.1 | 0 | 1.0 | 7.3 | 3.9 |
| 2D | 10 g | $CH_3CN$ | 120 | 28 | $K_2CO_3$ | 3.25 | 67.9 | 4.5 | 0.5 | 13.3 | 0 | 0.5 | 8.5 | 4.9 |
| 2E | 10 g | THF | 120 | 33 | $K_2CO_3$ | 3.25 | 58.6 | 20.1 | 1.2 | 9.9 | 0 | 0.4 | 7.2 | 2.5 |
| 2F | 10 g | DMF | 150 | 21 | Hünigs base + LiCl | 1.3 (1.3 of LiCl) | 49.5 | 5.1 | 29.5 | 11.7 | 4.4 | 0 | 0 | 0 |
| 2G | 10 g | DMF | 125 | 42 | $K_2CO_3$ | 5.0 | 69.8 | 9.5 | 1.6 | 7.1 | 0 | 4.2 | 7.1 | 0.7 |
| 2H | 5 g | DMF | 221 | na | $Li_2CO_3$ | 5.0 | 2.6 | 95.2 | 2.2 | 0 | 0 | 0 | 0 | 0 |
| 2J | 10 g | DMF | 130 | 17 | $K_2CO_3$ | 3.25 | 72.8 | 1.6 | 2.3 | 18.2 | 0.8 | 1.3 | 2.3 | 0.8 |
| 2K | 10 g | DMF | 120 | 17 | $K_2CO_3$ | 5.0 | 70.8 | 2.0 | 3.0 | 10.1 | 0 | 11.2 | 0 | 0.6 |
| 2L | 5 g | DMF | 150 | 22 | $K_2CO_3$ | 5.0 | 53.2 | 28.3 | 7.6 | 6.6 | 0.3 | 3.1 | 0.4 | 0.4 |
| 2M | 25 g | DMF | 120 | 30 | $K_2CO_3$ | 5.0 | 66.2 | 2.9 | 4.2 | 10.2 | 0.6 | 9.9 | 6.0 | 0 |
| 2N | 5 g | DMF | 140 | 22 | $K_2CO_3$ + LiCl | 5.0 (2.0 Of LiCl) | 52.1 | 37.8 | 2.9 | 5.4 | 0.2 | 0.4 | 1.2 | 0 |
| 2O | 25 g | DMF | 114 | 25 | $Na_3PO_4$ | 5.0 | 38.6 | 53.5 | 3.1 | 3.0 | 0.1 | 0 | 1.1 | 0.5 |
| 2P | 16.2 g | DMF | 111 | 3 | $K_2CO_3$ + LiCl | 3.25 (1.3 of | 71.6 | 1.8 | 1.8 | 18.2 | 0.4 | 3.0 | 2.3 | 0.9 |

TABLE 2-continued

| Ex. # | 1-Br-2,4-di-F—C$_6$H$_3$ | Solvent | Mol % allene | Init. Press. at 72° C. (psig) | Base | Mol % base | % I | % S.M. | % V | % VII | % VIII | % A | % B | % C |
|---|---|---|---|---|---|---|---|---|---|---|---|---|---|---|
| 2Q | 15.8 g | DMF | 110 | 3 | Na$_3$PO$_4$ (LiCl) | 3.0 | 73.6 | 10.9 | 5.2 | 7.4 | 0.3 | 0 | 2.0 | 0.7 |
| 2R | 10 g | acetone | 116 | 20 | Na$_3$PO$_4$ | 2.0 | 30.6 | 66.9 | 1.1 | 0.9 | 0 | 0 | 0.5 | 0 |
| 2S | 16.5 g | DMF | 120 | 3 | Na$_3$PO$_4$ | 5.0 | 78.1 | 4.3 | 4.5 | 7.7 | 0.3 | 0 | 3.2 | 1.8 |
| 2T | 12.2 g | DMF | 150 | 3 | Na$_3$PO$_4$ | 7.5 | 76.6 | 6.7 | 6.8 | 4.3 | 0.3 | 0 | 3.3 | 2.0 |

EXAMPLE 3

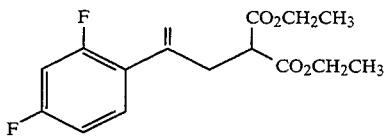

Wash 29 g (2 equiv.) of NaH (60% dispersion in oil) with heptane (2×80 mL). Combine the washed NaiI with 60 mL of DMF, then slowly add 11.0 g (68.8 mmol) of diethyl malonate while keeping the reaction temperature below 30° C. Stir the resulting mixture for 30 min to form a solution of diethyl sodiomalonate.

Combine 0.39 g of Pd$_2$(dba)$_3$, 0.34 g of dppe and 10 ml of DMF, in a suitable vessel and purge with nitrogen gas. Add 6.6 g of 2,4-difluorobromo-benzene and the sodiomalonate solution prepared above and cool the mixture to about −45° C. Charge the vessel with allene, then pressurize with nitrogen to 7.5 psi. Agitate the mixture at 55°–65° C. for 10 h. Cool to −45° C., add more allene, then agitate at 75°–80° C. for 24 h. Cool to room temperature, add allene and heat at 75°–80° C. for 4 h. Pour the reaction mixture into ice-cold water and extract with 300 mL of heptane. Filter, then dilute the heptane extract with 500 mL of EtOH. HPLC analysis of the resulting solution shows the presence of 7 g (86% yield) of the title compound. [HPLC analysis was carried out using a Zorbax®RX-C-8 column, 75:25 MeOH/water, 1 mL/min.] The title compound is isolated by concentration in vacuo.

EXAMPLE 4

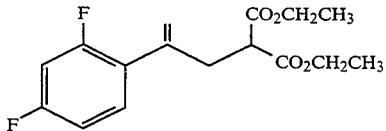

For purposes of comparison, 1-bromo-2,4difluorobenzene, sodio diethyl malonate and allene were reacted according to Procedure B as taught by Ahmar, et al, *Tetrahedron*, 43 (3), 513–526 (1987). The product was isolated and identified as the title compound contaminated by a 50% yield of the diene (V)

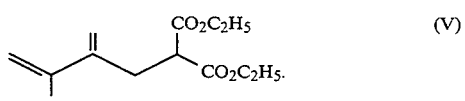

I claim:

1. A process for preparing compounds of the formula

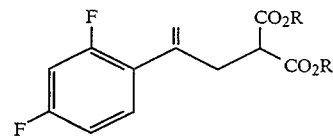

wherein R is C$_1$–C$_6$ alkyl, comprising heating a mixture of a difiuorobenzene derivative of the formula

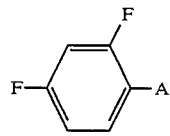

wherein A is Br, I, —OS(O)$_2$R$^2$, or —OP(=O)(OR$^3$)$_2$, and wherein R$^2$ is F, CF$_3$, C$_1$–C$_6$ alkyl, aryl or substituted aryl, and R$^3$ is C$_1$–C$_6$ alkyl, with allene, a dialkyl malonate of the formula CH$_2$(CO$_2$R)$_2$, wherein R is C$_1$–C$_6$ alkyl, and a base, in a polar organic solvent in the presence of a catalyst, in a sealed vessel and the pressure within the vessel is 1 to 10 psig.

2. The process of claim 1 wherein A is Br, R is ethyl or methyl, and the catalyst is a Palladium catalyst.

3. The process of claim 2 wherein the base is K$_2$CO$_3$, Na$_2$CO$_3$, NaH, KH, Na$_3$PO$_4$, K$_3$PO$_4$, or NaOR$^1$ or KOR$^1$, wherein R$^1$ is C$_1$–C$_6$ alkyl.

4. The process of claim 3 wherein the base is Na$_3$PO$_4$ or K$_3$PO$_4$.

5. The process of claim 4 wherein the solvent is DMF, DMSO, THF, acetone or acetonitrile.

6. The process of claim 5 wherein the mixture is heated to 40° to 120° C.

7. The process of claim 6 wherein the mixture is heated to 50° to 90° C.

8. The process of claim 1 wherein the catalyst is bis(diphenylphosphino)ethanepalladium(O), tetrakis(triphenylphosphine)-palladium(O), tetrakis(triphenylphosphine)-palladium(ll), chloride, or a combination of P(Ar)$_3$, wherein Ar is an aryl group selected from phenyl, and either tris(dibenzylideneacetone)dipalladium(O) or PdX$_2$, wherein X is Cl, Br or I.

9. The process of claim 8 wherein A is Br, R is ethyl or methyl, the base is K$_2$CO$_3$, Na$_2$CO$_3$, NaH, KH, Na$_3$PO$_4$, K$_3$PO$_4$, or NaOR$^1$ or KOR$^1$, wherein R$^1$ is C$_1$–C$_6$ alkyl, and the solvent is DMF, DMSO, THF, acetone or acetonitrile.

10. The process of claim 9 wherein the base is Na$_3$PO$_4$ or K$_3$PO$_4$.

11. The process of claim 10 wherein the mixture is heated to 40° to 120° C.

12. The process of claim 11 wherein the mixture is heated to 50° to 90° C.

13. The process of claim 12 wherein the mixture is heated to 70° to 80° C.

* * * * *

UNITED STATES PATENT AND TRADEMARK OFFICE
CERTIFICATE OF CORRECTION

PATENT NO. : 5,442,093
DATED : August 15, 1995
INVENTOR(S) : Anantha Sudhakar

It is certified that error appears in the above-indentified patent and that said Letters Patent is hereby corrected as shown below:

At Column 8, lines 51-52, delete the term

"tetrakis(triphenyl-phosphine)-palladium(II), chloride"

and insert in place therefor the term

-- bis(triphenylphosphine)palladium(II) chloride -- .

Signed and Sealed this

Thirty-first Day of October 1995

Attest:

BRUCE LEHMAN

Attesting Officer

Commissioner of Patents and Trademarks